United States Patent [19]
Carasso et al.

[11] Patent Number: 6,119,510
[45] Date of Patent: Sep. 19, 2000

[54] PROCESS FOR DETERMINING CHARACTERISTICS OF SUSPENDED PARTICLES

[75] Inventors: Melanie Carasso, Chatham; Sanjay Patel, New Providence; Jorge Luis Valdes, Branchburg; Christopher Alan White, Basking Ridge, all of N.J.

[73] Assignee: Lucent Technologies Inc., Murray Hill, N.J.

[21] Appl. No.: 09/143,435

[22] Filed: Aug. 31, 1998

[51] Int. Cl.$^7$ .......................... G01N 15/02; G01N 29/02; G01N 21/85

[52] U.S. Cl. ...................... 73/61.75; 73/24.02; 73/24.03; 356/437; 356/438; 356/441; 356/442

[58] Field of Search .................. 73/24.03, 24.02, 73/61.42, 61.75; 356/437, 438, 441, 442

[56] References Cited

U.S. PATENT DOCUMENTS

| | | |
|---|---|---|
| 3,779,070 | 12/1973 | Cushman et al. |
| 4,706,509 | 11/1987 | Riebel ..................................... 73/865.5 |
| 5,121,629 | 6/1992 | Alba ........................................ 73/61.41 |
| 5,569,844 | 10/1996 | Sowerby ................................. 73/61.75 |

FOREIGN PATENT DOCUMENTS

| | | | |
|---|---|---|---|
| WO91/07646 | 5/1991 | WIPO ................................. 73/61.41 |
| WO94/04907 | 3/1994 | WIPO ................................. 73/61.75 |

OTHER PUBLICATIONS

P. VanZant, *Microchip Fabrication*, 3$^{rd}$ Ed., McGraw–Hill, p. 300 (1997).

Epstein, P.S. and Carhart, R. R., "The Absorption of sound in suspensions and Emulsions", *J. Acoust. Soc. Amer.*, vol. 25, p. 553 (1953).

Allegra, J.R. and Hawley, S.A., "Attenuation of Sound in Suspensions and Emulsions: Theory and Experiments", *J. Acoust. Soc. Amer.*, vol. 51, p. 1545 (1972).

Mie, vonG., *Annalen Physik*, vol. 25, p. 377 (1908).

M. Kerker, *The Scattering of Light and Other Electromagnetic Radiation*, Academic Press (1969).

Guidarelli, G. et al., "Ultrasonic characterterisation of solid–liquid suspensions", *Ultrasonics,* GB, IPC Science and Technology Press Ltd., Guildford, vol. 36, No. 1–5, pp. 467–470 (1998).

Austin, J. C. et al., "Ultrasonic wave propagation in colloid suspensions and emulsions: recent experimental results" *Ultrasonics,* GB, IPC Science and Technology Press Ltd. Guilford, vol. 34, No. 2 pp. 369–374 (1996).

Chew, W.C. et al., "Effcient Computation of Three–Dimensional Scattering of Vector Electromagnetic Waves", *Journal of the Optical Society of Ameroca*–vol. 11, No. 4, pp. 1528–1537 (1994).

*Primary Examiner*—Daniel S. Larkin
*Attorney, Agent, or Firm*—Scott J. Rittman

[57] ABSTRACT

The invention provides an improved process for determining the characteristics of dispersed particles. The process involves directing waves (acoustic or light) into a dispersion, and measuring the attenuation of the waves for particular frequencies to provide an attenuation spectrum. The measured attenuation spectrum is then compared to a set of theory-based calculated attenuation spectra to determine the particle size distribution corresponding to the measured attenuation spectrum. Unlike previous processes, the particle size distribution is capable of being accurately determined by a single inversion algorithm, thus eliminating burdensome steps of previous methods.

12 Claims, 5 Drawing Sheets

PROCESS FOR DETERMINING CHARACTERISTICS OF SUSPENDED PARTICLES

BACKGROUND OF THE INVENTION

1. Field of the Invention

The invention relates to characterization of dispersed particles, e.g., determination of particle size distribution.

2. Discussion of the Related Art

Processes such as chemical-mechanical planarization (CMP) and sol-gel fabrication of silica bodies utilize dispersions of particles in a liquid medium. (For a discussion of CMP and sol-gel processes, see, respectively, P. Van Zant, *Microchip Fabrication,* 3rd Ed., McGraw-Hill, 300 (1997), and U.S. Pat. No. 5,240,488.) For such processes, it is desirable to know the specific properties of the particles. For example, larger particles in CMP often lead to scratches and variations in the median particle size and the size distribution sometimes lead to inconsistent polishing. Similarly, the properties of sol-gel derived bodies depend in large part on the characteristics of the particles in the dispersion. For these reasons, among others, various methods have been developed to determine the characteristics of particles in such dispersions.

One such characteristic is the particle size distribution (PSD). See, for example, U.S. Pat. Nos. 4,706,509, 5,121,629, and 5,569,844 (the '509, '629, and '844 patents, respectively). The '509 patent relates to a method for ultrasonically measuring solids concentration and particle size distribution in a dispersion. Ultrasonic waves at a variety of frequencies are directed into the dispersion, and the attenuation at the frequencies is measured. A dimensional spectrum (across the range of particle dimensions) is divided into dimensional intervals, and a system of linear equations is developed to represent the concentration of particles in each dimension interval. The system of equations is then solved to determine the PSD. However, the process of the '509 patent is limited to waves having a wavelength smaller than the largest particles. The process is therefore not useful for relatively fine particles, e.g., tens to hundreds of nanometers, since acoustic waves cannot presently be driven at the necessary frequencies.

The process of the '844 patent involves measuring the attenuation of both ultrasonic waves and electromagnetic radiation to determine particle size distribution. Specifically, ultrasonic velocity and ultrasonic attenuation are combined with the density, as determined from the electromagnetic radiation attenuation, to calculate the PSD. In addition to the problems inherent in generating x-rays or gamma rays, however, particle sizes of about 10 to 15 $\mu$m appear to be the lower limit for the process.

In the '629 patent, the disclosure of which is hereby incorporated by reference, ultrasonic waves at a variety of selected wavelengths are passed through a dispersion, and the attenuation at each frequency is measured to derive a measured attenuation spectrum over those frequencies. Separately, based on a theoretical model, a set of attenuation spectra are calculated for a variety of PSDs, and the calculated spectra are then compared to the measured spectrum to formulate a preliminary approximation of the PSD of the dispersion. Further calculations must be performed, starting from this approximation, to more accurately determine the PSD.

While current techniques for characterizing dispersed particles, e.g., determining PSD, are adequate for many purposes, improvements that provide more accurate, consistent, and reliable results are desired.

SUMMARY OF THE INVENTION

The invention provides an improved process for determining the characteristics of dispersed particles. (As used herein, the term particles includes solids, liquids, or gases dispersed in a continuous medium.) The invention involves directing waves (acoustic or light) into a dispersion, and measuring the attenuation of the waves for particular frequencies to provide an attenuation spectrum. (As used herein, waves includes, but is not limited to, continuous waves and pulsed measurments.) The measured attenuation spectrum is then compared to a set of theory-based calculated attenuation spectra to determine the particle size distribution corresponding to the measured attenuation spectrum. Unlike previous processes, the particle size distribution is capable of being accurately determined by a single inversion algorithm, thus eliminating burdensome steps such as those of the '629 patent, e.g. deriving a preliminary approximation of PSD, and going forward from the approximation through several inversion techniques. (Inversion techniques, in the present context, involve taking a set of known particle size distributions, determining the attenuation spectrum that each PSD would theoretically produce, and comparing a set of such theory-based spectra to the actual, measured spectrum to find the actual PSD.) By avoiding steps such as an initial approximation and a multi-step inversion technique, the invention produces more accurate, consistent, and reliable results.

In particular, while the process of the '629 patent provides useful results for some applications and some particle size distributions, the process has several potential drawbacks. The '629 patent starts with a well-known model for acoustic attenuation, which was set forth in Epstein and Carhart, *J. Acoust. Soc. Amer., Vol.* 25, 1953, 553, and revised by Allegra and Hawley, *J. Acoust. Soc. Amer., Vol.* 51, 1972, 1545, the disclosures of which are hereby incorporated by reference. From this model (referred to herein as the Allegra-Hawley model), a set of attenuation spectra are calculated for a set of known particle size distributions. When the actual attenuation spectra of a dispersion is measured, the '629 patent takes an initial guess of the PSD based on an initial comparison of the calculated spectra and measured spectrum (see Col. 15, lines 30–39). The quadratic discriminator (the first of three inversion techniques) then attempts to refine this initial guess by computing a limited number of attenuation spectra similar to the initial guess. Following the quadratic discriminator, the '629 patent uses the Powell discriminator, which selects a specific finctional form with a limited number of parameters, in an effort to speed the process of finding a match to the measured attenuation spectrum. However, this inversion technique may generate an inaccurate response when the selected functional form is not flexible enough to describe the shape of the true PSD. Finally, where the initial guess in the '629 patent indicates a narrow PSD, the impulse discriminator inversion technique is used, this third technique using linear equations to determine a PSD with effectively no spread in particle size. Unfortunately, the applicability of this third technique is limited. Specifically, because the impulse discriminator appears to be tailored toward specific systems, it has the potential to generate inaccurate responses when a variety of systems are tested. Moreover, the process of the '629 patent is tailored to acoustics, and would not be useful for light attenuation.

The invention overcomes these drawbacks of the '629 patent by application of a faster, more straightforward inversion technique. Specifically, the invention uses a single inversion algorithm that requires no prior knowledge (or guess) of the particle size distribution. Moreover, the single inversion algorithm is independent of the physical measurements being made relating to particle characteristics, i.e., the inversion technique is applicable to any model for predicting attenuation based on PSD, such as an acoustic attenuation model or a turbidity, i.e,, light attenuation, model. In one embodiment, an improved Allegra-Hawley model is used to calculate the set of theory-based acoustic attenuation spectra.

The single inversion algorithm involves parameterizing a particle size distribution, i.e., mathematically describing an abstract form such as a PSD based on a selected number of parameters. The parameters are then varied to obtain a "best" agreement between a measured spectrum and theoretical spectra, this best agreement providing the PSD. The best agreement is defined by minimization of an error function that is selected to not only incorporate the differences between measurement and theory, but to also weight each measured data point according to the confidence in that data. Unlike the '629 patent, no initial guess of the PSD is needed.

The invention therefore provides an improved process for determining the characteristics, particularly particle size distribution, of a particle dispersion, including a dispersion containing nanometer-size particles.

DETAILED DESCRIPTION OF THE DRAWINGS

Acoustic attenuation techniques for characterizing particles in dispersion involve the interaction of applied sound waves with the dispersed particles. As a sound wave travels through a dispersion, the wave loses acoustic energy by various scattering mechanisms. The total energy loss is given by the attenuation coefficient, $\alpha$ (dB/inch):

$$\alpha = \frac{1}{L}\ln\frac{I_0}{I_1} \quad (1)$$

where L is the path length across the dispersion, $I_0$ is the initial intensity of the sound wave, and $I_1$ is the intensity of the sound wave after passing through the dispersion. Measurement of the attenuation coefficient at different frequencies of the sound wave leads to an acoustic attenuation spectrum. The above-referenced models by Epstein and Carhart, and by Allegra and Hawley make it possible to predict the attenuation spectrum for particles of a given size distribution and concentration. The models require knowledge of several physical properties of the particles and the liquid medium, including density, thermal expansion coefficient, thermal conductivity, heat capacity, viscosity, and shear rigidity. It is then possible to construct a 3-D matrix that relates attenuation, frequency, and particle size.

Figure 1:
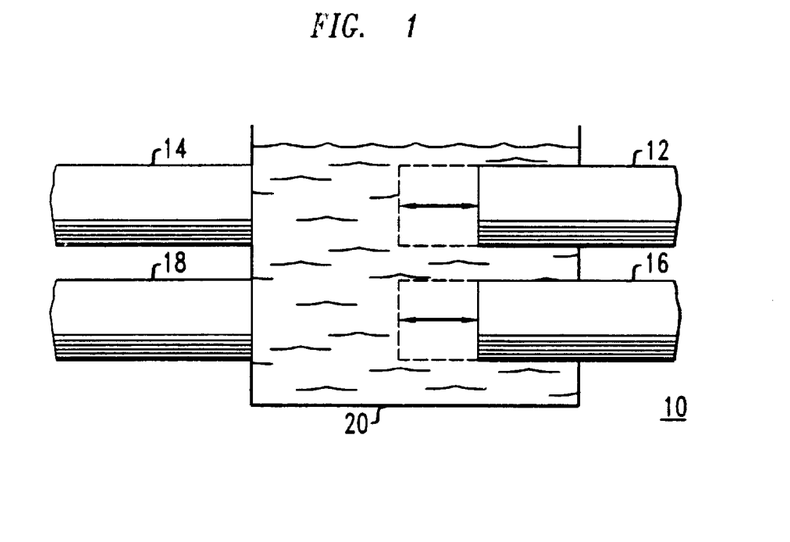
FIG. 1 schematically illustrates an apparatus useful in the invention.

Acoustic attenuation in a particle dispersion is measured by use of an apparatus such as the Ultrasizer™, made by Malvern Instruments, Ltd., Worcestershire, United Kingdom (who is also the assignee of U.S. Pat. No. 5,121,629, discussed above). A schematic of the chamber 10 of such an apparatus is shown in FIG. 1. Two pairs of broadband transducers 12, 14, 16, 18, are in contact with a sample located in a tank 20, typically formed of stainless steel. Advantageously, the transducers are designed to transmit a wave as close to a plane wave as possible. The chamber 10 typically contains a temperature sensor, heater, and a propeller (none of which are shown). It is possible to remove the sample by use of a drain valve at the base of the tank 20. Typically, one pair of transducers 12, 14 covers a lower frequency range, e.g., 1 to 20 MHz, and the other pair 16, 18 a higher range, e.g., 15 to 200 MHz. Generally, the transmitting transducers 12, 16 are capable of being moved to different positions in the chamber, but the receiving transducers 14, 18 are fixed. The spacing between the transmitting transducers 12, 16 and the receiving transducers 14, 18 is controlled by a stepper motor. The transmitting transducers 12, 16 direct a series of planar sound waves, generally at preselected frequencies, across the sample and the receiving transducers detect the attenuated waves. Computer and signal processing equipment, as apparent to one skilled in the art, is used to control the process of attaining the attenuation spectrum, monitor the detected sound waves, and manipulate the signals generated therefrom. As commercially available, the Ultrasizer™ provides both raw attenuation data as well as predicted particle size distributions. Other apparatus that measure attenuation, such as discussed in references cited in the Background section, are equally useful in the invention. Other commercially-available apparatus capable of being used in the invention include the CMP Slurry Monitor, made by Colloidal Dynamics, Inc. of Warwick, R.I., and the AcoustoPhor device, made by PenKem. It is also possible to use devices that utilize Fourier transform techniques to measure attenuation spectra. Advantageously, the apparatus is capable of being placed in-line in a production process, such that real-time measurements are provided.

Optical attenuation, or turbidity, measures the loss of intensity of light as it travels a fixed distance through a suspension. A turbidity spectrum is obtained by measuring attenuation at several wavelengths (frequencies) of light. The Mie theory describes the basic interaction between light and a dispersion of spherical particles. (See G. Mie, *Ann. Physik*, Vol. 25, 377 (1908). See also M. Kerker, *The Scattering of Light and other Electromagnetic Radiation*, Academic Press (1969).) The loss of intensity is directly related to the difference in refractive indices of the particle and the liquid medium, as well as to the particle size distribution. The attenuation mechanisms for light and sound differ greatly, making independent measurements by these techniques complementary.

The measurement of optical attenuation is able to be performed using a conventional ultraviolet-visible region (UV-Vis) spectrophotometer. Commercial units are available from several manufacturers such as Perkin-Elmer Corp., Spectral Instruments Inc., and Ocean Optics Inc. A basic device includes a broadband light source, a sample cell, a UV-Vis monochromator, and a photodetector. Light from the broadband source is collimated and directed through the sample cell. The light passing directly through the sample cell arrives at the monochromator, which directs a finite width of frequencies to the photodetector. By adjusting the monochromator, the light transmitted by the sample can be measured as a function of frequency. The log of the ratio of this spectrum to a standard reference is the UV-Vis attenuation or absorption spectra.

A variety of dispersions (solid, liquid, or gas particles in a continuous medium) are capable of being measured according to the invention. For example, it is possible to measure solid-in-liquid dispersions, such as silica, alumina, titania, or other oxides, in aqueous or non-aqueous media. It is also possible to measure emulsions (i.e., liquid particles in a continuous liquid medium), as well as liquid-in-gas and gas-in-liquid dispersions. The particle concentrations and particle diameters for which the invention will be functional are capable of varying widely, as long as a useful attenuation spectrum is obtained. Typical concentrations of particles that provide useful results range from 0.1 to 60 vol.%, more typically about 1 to 60 vol. %, and typical particle diameters range from about 1 nm to about 1000 $\mu$m, more typically about 10 nm to about 10 $\mu$m.

The invention involves directing waves (acoustic or light) into a dispersion, and measuring the attenuation of the waves for each particular frequency to provide an attenuation spectrum. The measured attenuation spectrum is then compared to a set of theory-based calculated attenuation spectra to determine the particle size distribution corresponding to the measured attenuation spectrum. The comparison is performed by a single inversion algorithm which requires no prior knowledge (or guess) of the particle size distribution, and which is independent of the nature of the physical measurements being made, e.g., acoustic or turbidity. The algorithm involves parameterizing a particle size distribution, and then varying the parameters to obtain a "best" agreement between measurement and theory, as defined by minimization of an error function that is selected to incorporate the differences between measurement and theory, and also weight each measured data point according to the confidence in that data. The minimization of this error function with respect to variations in PSD is capable of being performed through a conjugate gradient minimization procedure. The details of the process are as follows.

Inversion Technique (1) Parameterizing a particle size distribution

As discussed above, parameterizing involves mathematically describing an abstract form, such as a PSD, based on a selected number of parameters. In the invention, the particle size distribution is initially viewed as a completely general form, $\phi$ (x), which represents particles of varying size x. No assumptions or guesses as to the form of the PSD are made.

(2) Defining the Error

The error function, E, numerically describes the agreement between the theoretical and experimental spectra.

$$E = \int df\, fW(f)[P(f) - O(f)]^2 \quad (2)$$

Here, $f$ represents frequency, $W(f)$ is a weighting function, $P(f)$ is the predicted spectrum, and $O(f)$ is the observed experimental spectrum. This form is similar to a standard least-squares formulation where the square ensures non-negativity. Defining E as an integral over continuous functions rather than referring directly to the discrete frequencies of the experimental spectrum ensures that E's value remains independent of the details of the experiment (i.e. the number and location of the discrete frequency measurements).

The inclusion of the weighting function, $W(f)$, accounts for frequency dependent experimental uncertainty. For example, higher frequency data tends to include more experimental uncertainty (e.g., noise) than low frequency data. In such a case, giving the low frequency data more weight would emphasize the importance of differences in the low frequency data. Given a suitable standard, it is also possible to include instrumental variations within this weighting factor. Although the optimal $W(f)$ depends upon experimental conditions and the exact nature of the measurements, a nearly optimal form is obtained by weighting the data based upon the variation of the experimental data over several repeated measurements, $$W(f_j) = \frac{1}{\sigma_j^2} \quad (3)$$

where $\sigma_j$ represents such statistical variations, with j indicating particles in the dispersion.

The predicted spectrum, $P(f)$, is given by a linear combination of the attenuation from each particle within the distribution.

$$P(f) = \int dR\, A(f, R)\phi(R) \quad (4)$$

Although this predicted spectrum is an approximation (owing to non-linearities induced by multiple scattering phenomena), it provides desirable results in the invention. (The fact that this spectrum is an approximation, however, does not constitute an initial guess of PSD.) Within this approximation, the function $A(f,R)$ describes, in its entirety, the physical attenuation model. The function represents the attenuation at frequency f for a single particle of size R. By changing the form of this function, we can use this inversion method for both optical and acoustic attenuation.

Further, the treatment of models which are non-linear in $\phi(R)$, e.g., those for treating multiple scattering phenomena, may be accommodated by adding terms to Equation 4 representing higher powers of $\phi(R)$, without further changes to the invention.

Initially, as mentioned above, the particle size distribution is viewed as a completely general form, $\phi(R)$, unlike previous methods. A physically reasonable function form for $\phi(R)$, i.e., an initial approximation of the PSD, could be selected as in such previous methods. However, the invention avoids such an approximation in favor of a direct discretization of the above equations (discretization is the representation of a continuous function through the values of that function at discrete points). Therefore, $\phi(R)$ is represented as its magnitude at discrete values $\phi_j$, and thus the representation of $\phi(R)$ becomes increasingly complete as the number of discrete particle sizes treated increases.

(3) Computing the Error Function

Because the measurement of attenuation is performed at discrete frequencies, the computational treatment of this problem requires the discretization of the error function. In addition, because the attenuation data tends to be logarithmically spaced, the discretization is also desirably logarithmic. In this case, the integrals (Eqns. 2 & 4) become summations, $$E = \sum_i (\Delta lg f) f_i W_i [P_i - O_i]^2 \quad (5)$$

$$P_i = \sum_j (\Delta lg R) R_j A_{ij} \phi_j \quad (6)$$

where i represents frequency and represents particle sizes. Owing to the exponential ranges of frequencies and particle sizes, the terms of these summations may vary over several orders of magnitude. This means the accurate computation of E (and $P_i$) requires careful attention to round-off accumulation in the summations.

The representation of the theoretical model is contained within the matrix $A_{ij}$, which is optionally pre-computed for particular physical models, e.g. the acoustic attenuation of silica in water. This pre-computation allows the time-consuming portion of the process (i.e. model evaluation) to be performed independent of the measurement and inversion process. Since the experimental measurement defines the discrete frequencies of interest, the $A_{ij}$ used for a given inversion is often obtained through interpolation of a dense, pre-computed $A_{ij}$.

For a given experimental measurement, the discrete frequency values remain fixed throughout the inversion process. Thus, for computational speed, it is possible for the frequency summations to be pre-computed, leading to a more quickly computed error.

$$E = \sum_{jk} (\Delta lg R)^2 B_{jk} \phi_j \phi_k + \sum_j (\Delta lg R) C_j \phi_j + E_o \quad (7)$$

$$B_{jk} = \sum_i (\Delta lg f) f_i W_i (\Delta lg R)^2 A_{ij} A_{ik} \quad (8)$$

$$C_j = \sum_i (\Delta lg f) f_i W_i (\Delta lg R) A_{ij} O_i \quad (9)$$

$$E_o = \sum_i (\Delta lg f) f_i W_i O_i O_i \quad (10)$$

Although these equations are formally identical to Equation 5, numerical round-off leads to computational differences. The invention uses both forms of the error expression to balance speed and accuracy.

(4) Minimizing the Error

The determination of the particle size distribution requires minimization of the error function with respect to variations in the $\phi_j$. Physically, the particle size distribution must be non-negative for all particle sizes. This introduces constraints on the possible variations in the $\phi_j$. To remove this constraint, the invention introduces another set of variables $c_j$ such that $$\phi_j = (c_j)^2 \quad (11)$$

This ensures the $\phi_j$ are non-negative. Thus, instead of requiring a difficult constrained minimization on $\phi_j$, it is possible to perform a simple unconstrained minimization on the independent, unconstrained $c_j$.

The minimization begins with an unbiased starting distribution where all $c_j$ are zero. To speed convergence from this starting point, several sub-minimizations are performed. The sub-minimizations correspond to coarse discretizations of the $\phi(R)$. For example, it is possible for the first sub-minimization to divide the range of possible particle sizes into 50 discrete values. Upon reaching a suitable minimal error for this sub-minimization (defined when the gradient of the error is below a chosen tolerance), the number of discrete values is increased (e.g. to 100 particle sizes). The information from a previous sub-minimization is used as an initial starting point for subsequent minimizations. This process continues until the final discretization level is achieved. This allows the code to quickly select a region of particle sizes in the early sub-minimizations, which is further refined in future minimizations.

For this minimization, the invention employs a conjugate gradient minimization using exact line searches. The search directions are accurately computed using the gradient of Equation 5. The line search is quickly processed using the gradient of Equation 7. It is possible that scaling of the gradient, or other pre-conditioning, will increase the speed of the minimization.

Attenuation Model

As mentioned above, the inversion technique of the invention is independent of the physical measurements being made to characterize the particles. Thus, there are at least two models capable of being combined with the inversion technique to determine particle size distributions. The first model is that initially developed by Epstein and Carhart, referenced above, relating to acoustic attenuation of water droplets in fog, and then further developed by Allegra and Hawley in the context of solid spherical particles in continuous liquid media. However, to improve the results obtained by the invention, several modifications have been made to this standard Allegra-Hawley formulation (referred to as improved Allegra-Hawley). These modifications concern what is believed to be an unjustified approximation for the treatment of solid particles, as well as several smaller changes to the form of the equations necessary to obtain a numerically stable and thermodynamically consistent computational method. Although each of these changes is easily understood by one skilled in the art of numerical computing, it is important to note that, without such careful attention to numerical stability and round-off, the invention would not perform as well.

Many of the modifications to Allegra-Hawley are computational rather than mathematical. The large ranges of particle size, frequency, and attenuation apparent for the acoustic measurements require careful attention to numerical stability. The basic computational task of obtaining a theoretical attenuation spectrum requires the formation of a set of coefficients and the solution of a set of coupled linear equations. The computation of these coefficients requires the evaluation of several auxiliary functions of complex argument. Care must be taken that these functions are reliably computed over the range of arguments necessary. Also, the standard numerical tasks of minimizing round-off and ensuring the linear equation solver is robust and stable are important for correct computation of theoretical spectra. This attention to detail allows the invention to compute numerically correct attenuation spectra for, at a minimum, particles ranging in radius from 5 nm to 10 $\mu$m and for frequencies from 100 kHz to 200 MHz. The approximations inherent in the physical model, rather than numerical issues, tend to increase the potential for errors as these ranges are extended.

Thermodynamics provides exact relationships between the physical properties of a material system. Thermodynamic consistency refers to methods which maintain these exact relationships. For computational methods, thermodynamic consistency is manifested as stability with respect to minor changes in input physical properties. With the Allegra-Hawley formulation, researchers have found the computed attenuation spectrum to be very sensitive to small changes in the input quantities. By re-deriving the equations using quantities that remain thermodynamically consistent, our computational method does not show these sensitivities to such input properties. One important example of obtaining thermodynamic consistency concerns the relationship between the specific heat ratio, the isothermal compressibility, and the speed of sound. The specific heat ratio, $\gamma$, is determined by the speed of sound q, the coefficient of thermal expansion $\beta$, the temperature T, and the specific heat at constant pressure $C_p$.

$$\gamma = 1 + \frac{q^2 \beta^2 T}{C_p} \quad (12)$$

The isothermal compressibility $\kappa$, is determined by the speed of sound, the specific heat ratio, and the density $\rho$.

$$\kappa = \frac{\gamma}{q^2 \rho} \quad (13)$$

These two equations provide an exact relationship between $\gamma$, q, and $\kappa$. It is possible, however, that independent experimental determinations of $\gamma$, q, and $\kappa$ will not satisfy these equations exactly. Small deviations away from these exact relationships become important since these quantities enter the final equations as the difference of two large numbers. Thermodynamic consistency is achieved by using numerically stable intermediates satisfying the constraints inherent in the exact relationships.

As an illustration, Table 1 shows the average changes in the theoretical acoustic attenuation (for R=5 nm to 10 $\mu$m; and for f=1 MHz to 150 MHz) given a ±10% change in each physical property. These resulting changes in attenuation are small relative to the range of measured attenuations, and this table therefore illustrates the stability of the invention with respect to changes in input properties, where this stability is due to the re-derivation of the model's equations. As expected, the table also shows that the viscosity, density, and speed of sound are the most important physical characteristics of the system for predicting attenuation. The stability in attenuation provided by the invention's use of an improved Allegra-Hawley leads to a more accurate determination of particle size distribution.

TABLE 1

| | Property ↓ | Atten. (+10% change in property) | Change (−10% change in property) |
|---|---|---|---|
| Particle: | Specific Heat | 0.1% | 0.1% |
| | Density | 15.1% | 18.0% |
| | Speed of Sound | 0.3% | 0.4% |
| | Thermal Dilation | ~0.0% | ~0.0% |

TABLE 1-continued

| | Property ↓ | Atten. (+10% change in property) | Change (−10% change in property) |
|---|---|---|---|
| | Lame Coefficient | 0.1% | 0.0% |
| | Attenuation (pure) | ~0.0% | ~0.0% |
| Liquid: | Specific Heat | 0.1% | 0.1% |
| | Density | 19.2% | 18.4% |
| | Speed of Sound | 12.0% | 10.3% |
| | Thermal Dilation | 0.1% | 0.1% |
| | Viscosity | 4.3% | 5.0% |
| | Attenuation (pure) | 0.8% | 0.7% |

Figure 2:
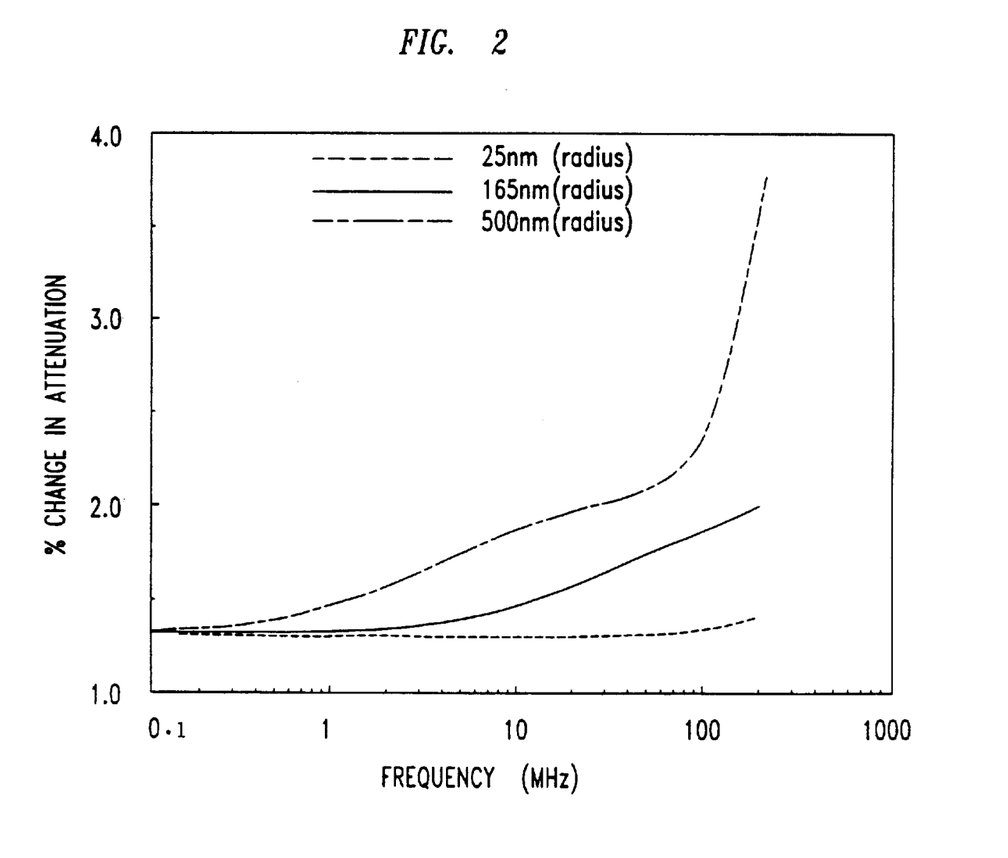
FIG. 2 illustrates the improvements made in the Allegra-Hawley model, according to the invention.

The improved Allegra-Hawley is also based on the following: The standard Allegra-Hawley formulation defines the compressional wavevector $k_c$ as $$k_c = \frac{\omega}{q} + i\alpha_L \quad (14)$$

where $\omega$ is the applied frequency, q is the speed of sound, and $\alpha_L$ is the acoustic attenuation for the pure substance. This expression is obtained by neglecting second order terms when decoupling the compressional and thermal wave equations. While this approximation is justified in the case of liquids or gases (as in Epstein & Carhart's work), for solids this approximation incorrectly computes the compressional wavevector. Fortunately, this approximation is easily removed from the standard formulation by computing the compressional and thermal wavevectors exactly, including second and higher terms. FIG. 2 displays the effect (in percentage change in attenuation) of removing this approximation from the computed attenuation spectra for three particle sizes (radii of 25 nm, 165 nm, and 500 nm). The effect is larger for larger particles at higher frequencies. Because the change in attenuation varies with frequency, this error would lead to improper inversions.

The second model useful in the invention relates to turbidity, which is the attenuation of light, and was initially presented by G. Mie, *Ann. Physik*, Vol. 25, 377 (1908). See also M. Kerker, *The Scattering of Light and other Electromagnetic Radiation*, Academic Press (1969). This model is capable of being successfully used in the invention without any modifications.

The invention will be further clarified by the following examples, which are intended to be exemplary.

EXAMPLE 1

Figure 3A:
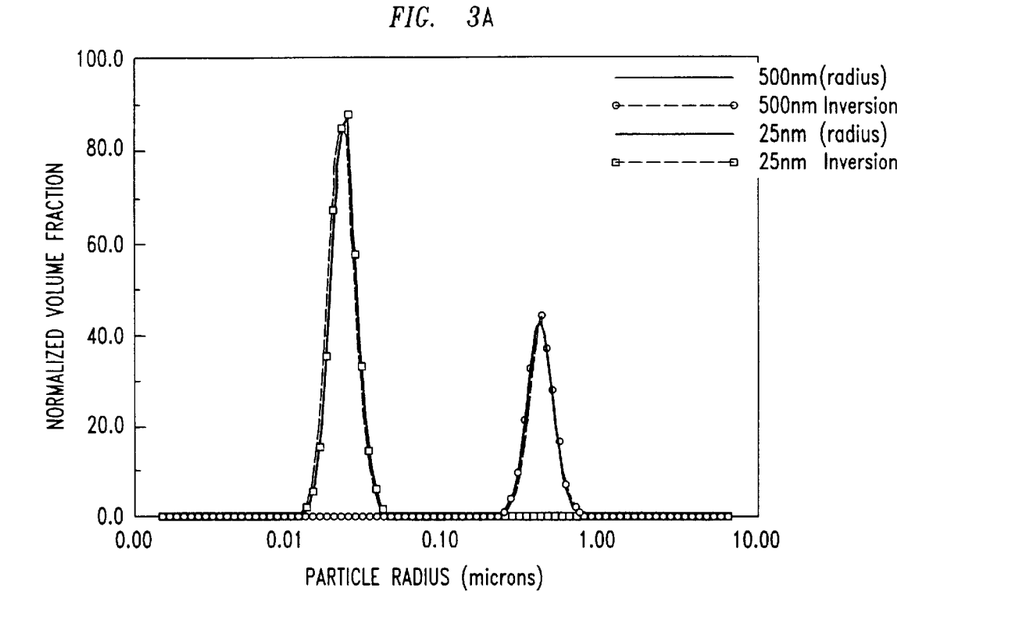
FIGS. 3A and 3B show particle size distributions generated according to the invention from simulated acoustic attenuation spectra.

The inversion technique and the model were first tested in the absence of experimental error using a set of simulated attenuation spectra. The simulated spectra were obtained from the acoustic attenuation model for two log-normal particle size distributions ($\mu$=25 nm (radius), $\sigma$=0.005; $\mu$=500 nm (radius), $\sigma$=0.1) The inversion process, when applied to the simulated spectra, generates a particle size distribution which may be directly compared with the assumed distributions. FIG. 3A shows the assumed and computed distributions for both the 25 nm radius and the 500 nm radius tests. The invention was able to reproduce both the median radius and width of the assumed distributions accurately over a broad particle size range.

Figure 3B:
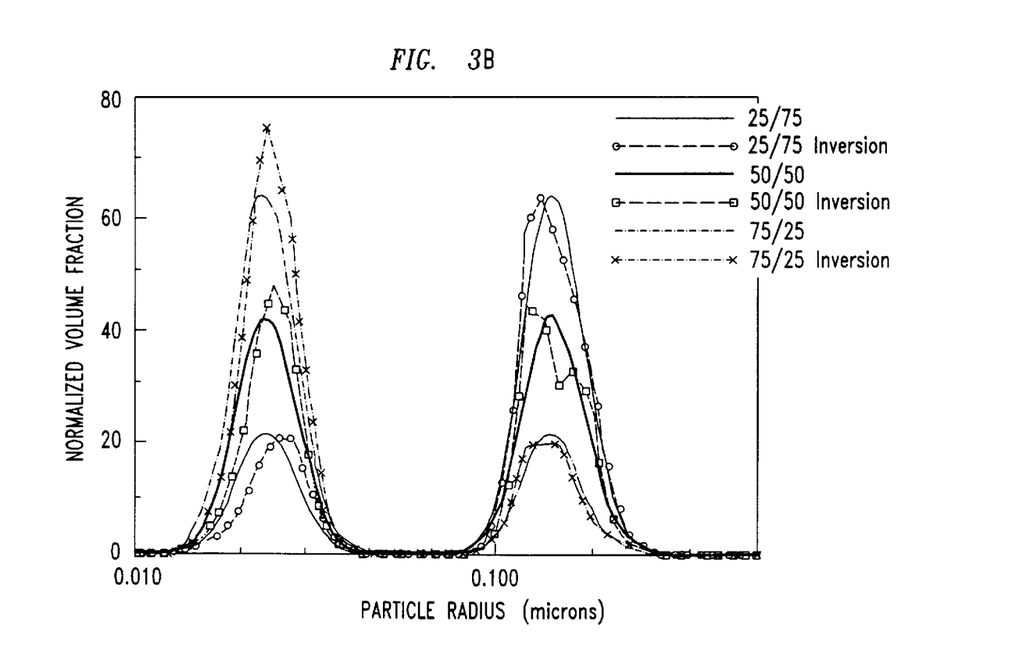

Simulated spectra were also used to test the sensitivity of the invention toward the presence of more than one population of particle size. FIG. 3B shows a set of particle size distributions obtained by inverting simulated spectra for three different mixtures of 25 nm radius and 165 nm radius particles (again superimposed on the assumed distributions). The ratios in the Figure refer to the volume percentages of 25 nm radius and 165 nm radius particles, respectively, in each mixture. The two populations of particle sizes were distinguished clearly by the invention, and the relative proportions and widths of the distributions were reproduced with reasonable accuracy.

EXAMPLE 2

Figure 4A:
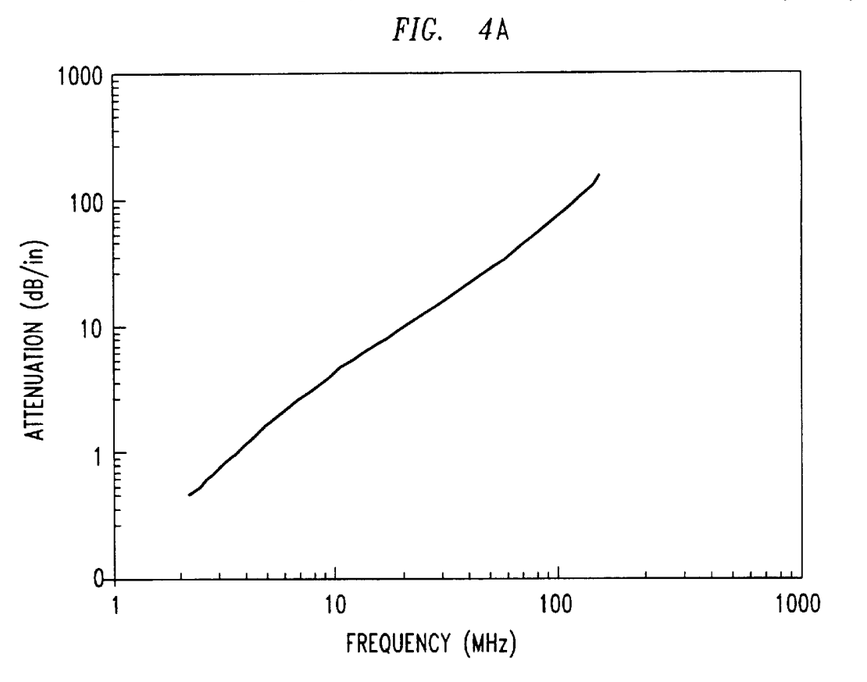
FIGS. 4A and 4B show, respectively, measured acoustic attenuation data and a particle size distribution generated from the data by the process of the invention.
Figure 4B:
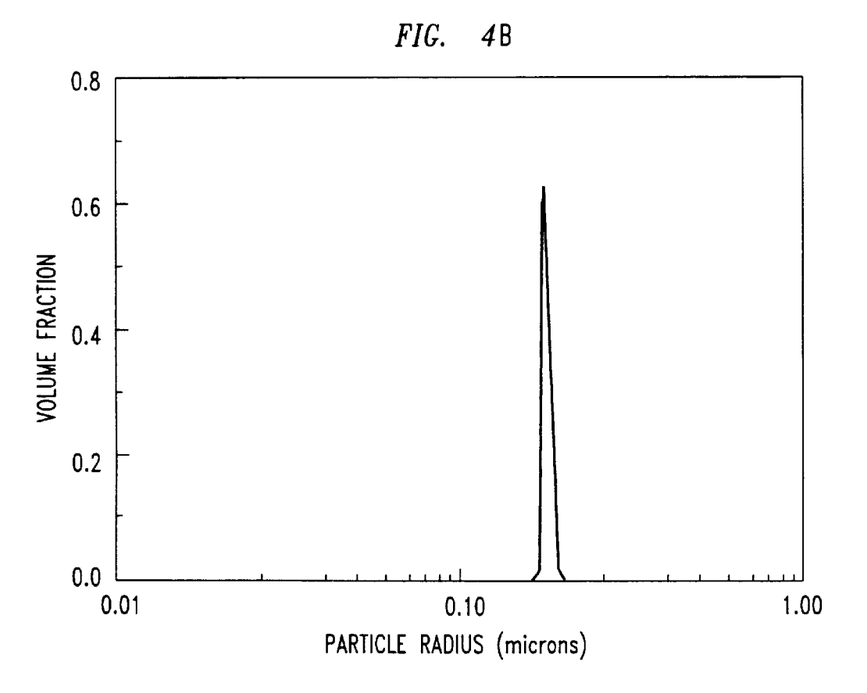

An acoustic attenuation spectrum was measured for a 1 vol % suspension of silica particles (MP4030, Nissan Chemical Corp., Tokyo) using an UltrasizerM (Malvern Instruments Ltd., Worcestershire, U.K.). The tested Nissan particles are often used as a reference material for sizing instruments, having a nominal diameter of 300 nm and a relatively narrow size distribution. The sample was stirred at 150 rpm with a stainless steel propeller, and the temperature was 25° C. The automatic optimal strategy feature of the Ultrasizer™ was used to determine the most effective frequency range and transducer spacings for the attenuation measurements. FIG. 4A shows the measured attenuation spectrum. The resulting particle size distribution determined by the inversion technique of the invention is shown in FIG. 4B. The particle radius (~0.165 μm) was accurate, and the spread of the distribution was narrow, as expected.

EXAMPLE 3

Acoustic attenuation measurements were made on commercially available chemical mechanical polishing (CMP) slurries. Kebosol 30N50 and Kiebosol 30N25 (Solution Technology, Inc., Monroe, NC) are 30 wt % silica slurries in ammonia solution, with nominal particle diameters of 50 nm and 25 nm respectively. The 30N50 and 30N25 slurries were each diluted to 5 vol % in water and measured separately in an Ultrasizer™, under the experimental conditions described in Example 2.

Figure 5A:
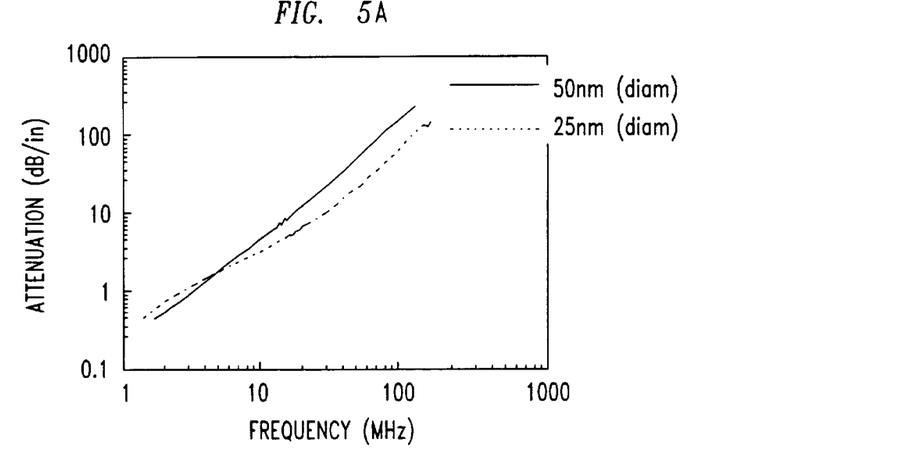
FIGS. 5A–5C show, respectively, measured acoustic attenuation data, a is particle size distribution generated from the data by a previous method, and a particle size distribution generated from the data by the process of the invention.
Figure 5B:
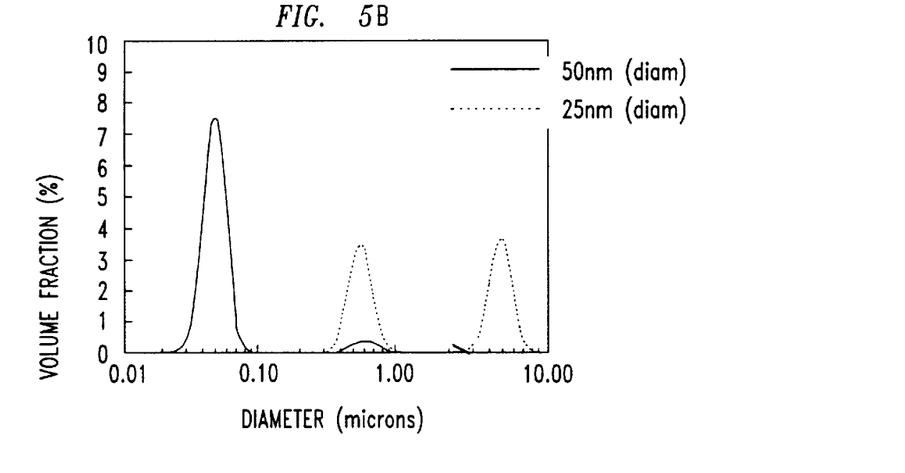

The acoustic attenuation spectra from the Ultrasizer™ for the two samples are plotted in FIG. 5A. The reproducibility of these spectra was high, with a variance of less than 5% over 60 measurements on each sample. The resulting particle size distributions determined by the Ultrasizer™ software are shown in FIG. 5B. These size results were obtained using the default values for the geometric standard deviation (narrowest allowed deviation=1.2, broadest allowed deviation=3.0) and the default number of iterations (15 iterations). The default model for the size distribution (a linear combination of two log-normal distributions) was used. Despite a low reported fit error, the 25 nm slurry gave misleading size results (of about 500 nm and about 5 μm) and the estimated concentration (0.8 vol %) was inaccurate. The 50 nm sample showed a first mode with mean diameter 41 nm containing 95% of the particle population, with a second mode of mean diameter 540 nm.

Figure 5C:
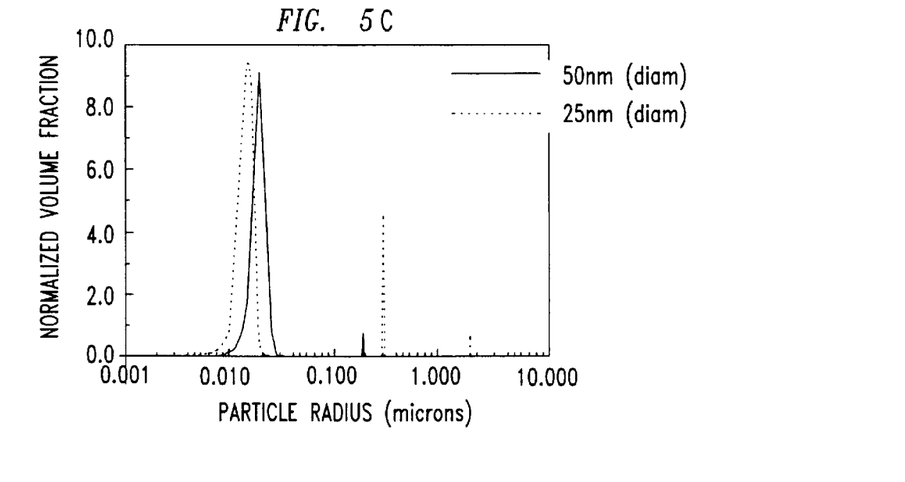

FIG. 5C shows the particle size distributions determined by the invention for the measured attenuation spectra (FIG. 4A). For both slurries, the main size mode occurred in the vicinity of the nominal particle radius. Narrow peaks with small populations were also apparent for both slurries at larger particle sizes.

EXAMPLE 4

Figure 6A:
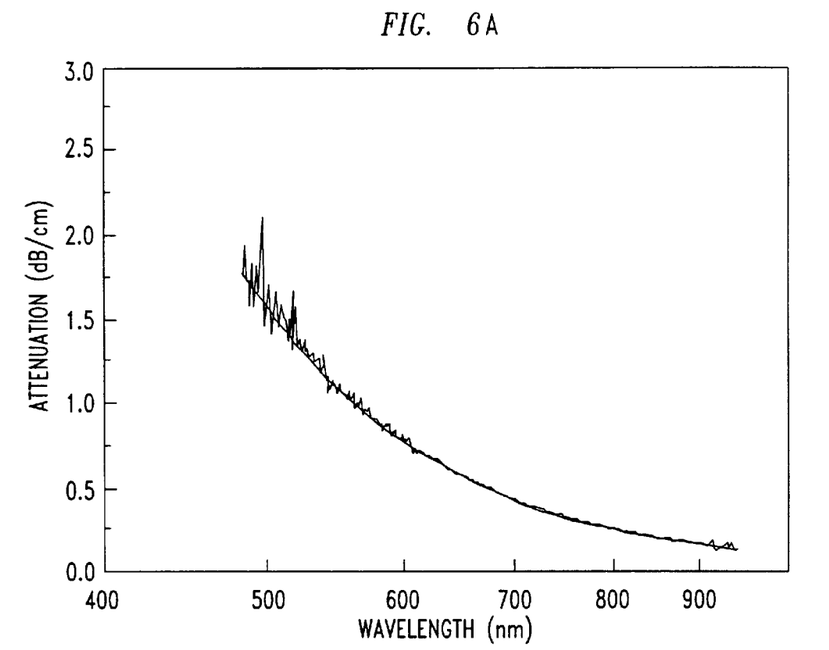
FIGS. 6A and 6B show, respectively, raw turbidity data and a particle size distribution generated from the data by the process of the invention.
Figure 6B:
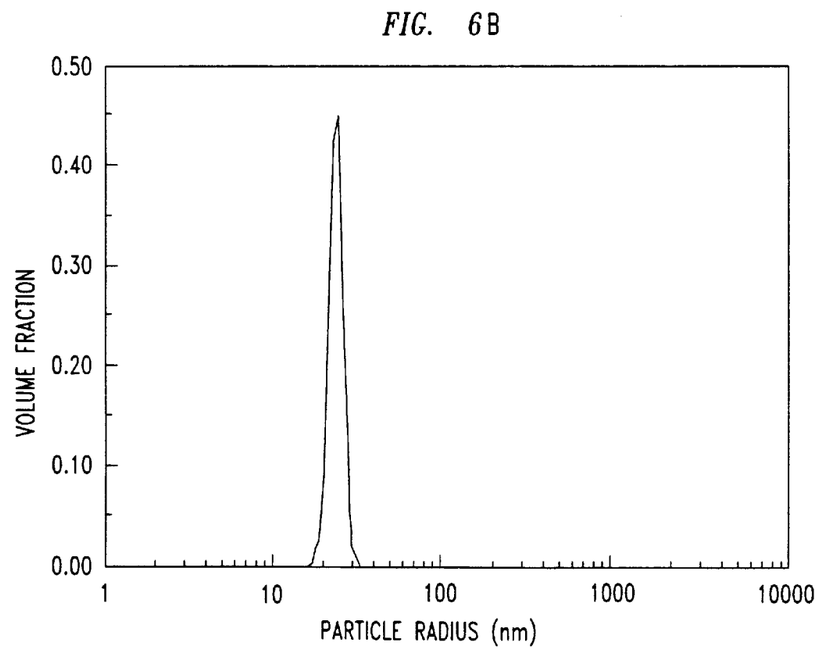

Turbidity measurements were made using an Ocean Optics S2000 spectrometer (Ocean Optics Inc., Dunedin, Fla.) and a tungsten-halogen light source. The dark current of the photodetector was measured and subtracted from all experimental measurements. The attenuation spectrum of water was used as a reference spectrum for the attenuation measurements of the suspensions. FIG. 6A is an example of a measured turbidity spectrum for 50 nm diameter silica particles at 1 vol % (KIebosol 30N50, Solution Technology Inc., Monroe, N.C.). The smooth curve is the theoretical fit to the experimental data. Strong absorption (e.g., in the UV region for silica particles) limits the usable wavelength range in dense suspensions. However, it was found that the 500–900 nm wavelength range was sufficient for the inversion process. The particle size distribution determined by the invention for this turbidity spectrum is shown in FIG. 6B. The mean particle radius of 21 nm was in accord with the nominal size, and the size spread was narrow.

Other embodiments of the invention will be apparent to those skilled in the art from consideration of the specification and practice of the invention disclosed herein.

What is claimed is:

1. A process for determining the characteristics of particles dispersed in a medium, comprising the steps of:

directing waves into a dispersion;

measuring the attenuation of the waves for particular frequencies to provide an attenuation spectrum;

performing an inversion technique to determine the particle size distribution corresponding to the measured attenuation spectrum, wherein the inversion technique involves comparing the measured attenuation spectrum to a set of theory-based calculated attenuation spectra, and wherein the inversion technique is performed in the absence of a step of deriving a preliminary approximation of the particle size distribution.

2. The process of claim 1, wherein the comparison step and the determination of particle size distribution are performed by a single inversion algorithm.

3. The process of claim 1, wherein the comparison step and the determination of particle size distribution are capable of being performed with no prior knowledge of particle size distribution.

4. The process of claim 1, wherein the waves are selected from acoustic waves and light waves.

5. The process of claim 4, wherein the waves are acoustic waves and the theory-based attenuation spectra are calculated from an improved Allegra-Hawley model.

6. The process of claim 4, wherein the waves are light waves and the theory-based attenuation spectra are calculated from the Mie model.

7. The process of claim 1, wherein the particles range in diameter from about 1 nm to about 1000 μm.

8. The process of claim 7, wherein the particles range in diameter from about 10 nm to about 10 μm.

9. The process of claim 1, wherein the particles are present in an amount ranging from 0.1 to 60 vol. %.

10. The process of claim 1, wherein the step of comparing comprises:

computing an error function based on comparison between the measured attenuation spectrum and the calculated attenuation spectra; and minimizing the error function.

11. The process of claim 10, wherein the minimization is performed by conjugate gradient minimization.

12. The process of claim 10, wherein at least a portion of the computed error function is pre-computed prior to directing the waves into the dispersion, based on the physical properties of the dispersion.

* * * * *